US006196227B1

(12) United States Patent
Tsushima

(10) Patent No.: US 6,196,227 B1
(45) Date of Patent: Mar. 6, 2001

(54) WATER SOLUBLE LUBRICANT FOR A CONDOM AND A CONDOM SPREAD WITH SAID WATER SOLUBLE LUBRICANT

(75) Inventor: Kyogo Tsushima, Ryuugasaki (JP)

(73) Assignee: Okamoto Industries INC, Tokyo (JP)

( * ) Notice: Subject to any disclaimer, the term of this patent is extended or adjusted under 35 U.S.C. 154(b) by 0 days.

(21) Appl. No.: 08/996,208

(22) Filed: Dec. 22, 1997

(30) Foreign Application Priority Data

Dec. 20, 1996 (JP) .................................................... 8-340909
Apr. 28, 1997 (JP) .................................................... 9-110521

(51) Int. Cl.$^7$ ........................................................ A61F 6/04
(52) U.S. Cl. .............................................................. 128/844
(58) Field of Search ...................................... 128/844, 845

(56) References Cited

U.S. PATENT DOCUMENTS 5,785,054 * 7/1998 Kelly ..................................... 128/842
5,800,412 * 9/1998 Zhang et al. .......................... 604/280
5,858,340 * 1/1999 Briggs et al. ....................... 424/70.19

\* cited by examiner

*Primary Examiner*—Kim M. Lems

(57) ABSTRACT

A water soluble lubricant for condoms includes at least a sliminess agent and a penetrating agent, and optionally, a humectant. The water soluble lubricant has a good penetrating feature to the wound up part of a condom, does not whiten the surface appearance of a condom, and provides sliminess and wettability to a condom to which the lubricant is applied. Water soluble penetrating agents which have good penetrating effect to the wound up part and do not whiten the appearance of a condom include sodium-lactate and trimethylglycine. Humectants which provide a condom with good wettability include glycerin and propyleneglycol. The water soluble sliminess agent which provides a condom with sliminess may be pullulan.

12 Claims, No Drawings

WATER SOLUBLE LUBRICANT FOR A CONDOM AND A CONDOM SPREAD WITH SAID WATER SOLUBLE LUBRICANT

BACKGROUND OF THE INVENTION

The present invention relates to a water soluble lubricant which is used for a condom and a condom whose surface is spread with said water soluble lubricant.

DESCRIPTION OF THE PRIOR ART

As a lubricant to be applied to a condom, the lubricant which satisfies following two items is required. Namely, a property to penetrate easily into a wound up part of condom after it is dropped on a wound up part of condom, and a sliminess property when it is used. In general, a lubricant which has an excellent slipping ability is ranked with a good lubricant, however, as a lubricant for condom, a lubricant which merely has a slipping ability is not required, but a lubricant which has adequate sliminess and appropriate slipping resistance is required. That is, the lubricant which has low static friction, high dynamic friction after starting to slip and appropriate slipping resistance is required. In this invention, the mentioned physical property is called sliminess. Further, it is required that a lubricant for condom penetrate into a wound part of the condom homogeneously when it is applied to the wound up part and furthermore required to provide a condom with a wettability. These effects can be generated by the combined use of two or more kinds of lubricant.

Presently, a silicone oil is mainly used as a lubricant for a condom. Silicone oil is applied to a condom. However, since silicone oil is a lipophilic agent and is not water soluble, it has a problem that it is very hard to be removed when it is adhered to a skin or clothes.

To solve this problem, many kinds of water soluble lubricants are proposed. However, most of these proposed lubricants, when applied to a condom, have a tendency to whiten the condom by water absorption and not only affect the appearance but also deteriorate the properties of the condom.

The lubricant which is applied to a condom disclosed in Japanese Patent Laid open publication 7-267849 is one approach to solve the problem. The feature of the invention disclosed in this publication is to add squalane to the lubricant. Squalane differs from the conventional silicone oil, which has slimy touch, and is superior at lubrication and humidity, provides a comfortable touch because of it's water solubility, does not whiten a condom and does not affect the physical property of a condom. However, since the squalane blended lubricant for condom has the following problem, squalane is not a satisfactory lubricant. That is, the lubricant does not easily penetrate into a wound up part of condom and the rubber film adheres tightly, so it becomes hard to unwind it at the time of actual use.

Further, the squalane blended lubricant for condom can improve the sliminess by increasing the viscosity, however, a threading phenomenon occurs along with the increase of viscosity and deteriorates the appearance of condom as a commodity. Therefore, this lubricant can not be used as a sliming agent.

OBJECT OF THE INVENTION

The present invention is carried out to solve the above mentioned problem. The object of this invention is to provide a water soluble lubricant for condom which can be easily removed by water when adhered to a human skin, which does not occasion the whitening phenomenon of a condom by water absorption and which has a good penetrating property into a wound up part of a condom, gives a condom with a sliminess at the actual use, moisturizes a condom and improves a wettability. And another object of this invention is to provide a condom whose surface is spread with said water soluble lubricant.

BRIEF SUMMARY OF THE INVENTION

As above mentioned, the object of this invention is to provide a lubricant for condom which penetrates easily into the wound up part of condom and gives a condom with a sliminess at the actual use, and another object of this invention is to provide a lubricant for condom which improves the wettability of a condom and moisturizes a condom, and a lubricant for condom which penetrates easily into the wound up part of condom.

Further, the other object of the invention is to provide a condom whose incompatibility during actual use is improved to have a natural feeling by coating the condom with above mentioned lubricant for condom.

The above mentioned objects are accomplished by the following water soluble lubricant for condom and by a condom whose surface is spread with said water soluble lubricant. Namely, as the water soluble lubricants which are superior at the penetration to the wound up part of a condom and do not whiten the appearance of a condom, one or more kinds of aqueous solution of agents selected from sodium lactate, trimethylglycine, sodium dl-malate, monosaccharide and salts of dl-pyrrolidonecarboxylic acid can be mentioned.

As the water soluble lubricant which provide a condom with sliminess, at least one kind of aqueous solution of agents selected from the group listed below can be mentioned. That is: pullulan, ammonium-polymethacrylate, sodium-starch-glycollic acid, polyvinylpyrrolidone, xanthane gum, guar gum, gellan gum, tamarindo gum, tarra gum, locust bean gum, arabian gum, sodium alginate, propylene glycol alginate, karaginane, sodium-carboxymethylcellulose, dextran, furcelleran and sodium polyacrylate.

Further, as a humectant which moisturizes a condom, at least one humectant selected from glycerin, propyleneglycol and polyethyleneglycol having 200 to 600 weight average molecular weight can be mentioned.

And further, the present invention provides a condom on whose surface is spread said water soluble lubricant. As a lubricant to be applied to a condom, a lubricant composed by an agent which has good penetration to the wound up part of a condom (this kind of lubricant is simply called a penetration agent) and an agent which provides a condom with sliminess (this kind of lubricant is simply called a sliming agent), and, optionally, an agent which provides a condom with a wettability (this kind of lubricant is simply called a humectant) can be used.

DETAILED DESCRIPTION OF THE INVENTION

Referring to the lubricant for condom of this invention, in the lubricant composed by a water soluble lubricant which protects a condom from whitening and a lubricant which provides a condom with sliminess, as a monosaccharide to be used as a penetration agent, xylose, glucose and fructose are preferably used and when these kinds of monosaccharide are used alone, the desirable water content is 40–80 wt %.

When water content is smaller than 40% penetration is not sufficient, and when water content is bigger than 80% the surface of condom becomes white. In a case of water soluble lubricant which provides a condom with sliminess, less than several % of refined water is added to sliming agent. The viscosity of obtained aqueous solution is, for instance; in a case of xanthan gum, from 400 to 10,000 centi Poise; in a case of guar gum, from 200 to 30,000 centi Poise; in a case of gellan gum, from 5,000 to 40,000 centi Poise; in a case of tamarindo gum, from 400 to 20,000 centi Poise; in a case of locust bean gum, from 400 to 60,000 centi Poise; and in a case of pullulan, from 5 to 400 centi Poise, and it is desirable to control the viscosity of each aqueous solution in above mentioned limit.

As a humectant agent, glycerin, propyleneglycol and polyethyleneglycol having 200 to 600 weight average molecular weight are preferably used, and usually these are used alone or used together.

Further, the inventors of the present invention have conducted many intensive experiments based on many kinds of knowledge to obtain a water soluble lubricant for condom which is superior at easy penetration into the wound up part of condom and having good wettability and sliming feature, and confirmed that such kind of a water soluble lubricant for condom can be obtained by mixing use of the following agents. That is, a penetration agent which has an excellent penetrating ability to the wound up part of a condom and does not whiten the appearance of the condom, and a sliming agent which provides a condom with a sliminess property are mixed together with a desirable mixing ratio under the conditions mentioned below.

Namely, as the penetration agent, a mixture of one or more kinds of aqueous solution of agent selected from a group composed by sodium lactate, trimethylglycine, sodium dl-malate, monosaccharide and salts of dl-pyrrolidonecarboxylic acid is used, and as the water soluble sliming agent, a mixture of one or more kinds of aqueous solution of agent selected from the group composed by pullulan, ammonium-polyacrylate, ammonium-polymethacrylate, arabian gum, dextran, tamarindo gum, furcelleran, sodium-starch-glycollic acid, sodium-polyacrylate, polyvinylpyrrolidone is used.

As the water soluble lubricant, it is confirmed that an excellent lubricating effect can be obtained by using main aqueous solution of sodium lactate and dissolving one or more kinds of aqueous solution of agent selected from the group composed by ammonium-pplyacrylate, ammonium-polymethacrylate, arabian gum, polyvinylpyrrolidone, dextran and pullulan to the main aqueous solution.

As the water soluble lubricant, it is confirmed that an excellent lubricating effect can be obtained by using main aqueous solution of trimethylglycine and dissolving at least one kind of aqueous solution of agent selected from a group composed by arabian gum, dextran and pullulan to the main aqueous solution.

As the water soluble lubricant, it is confirmed that an excellent lubricating effect can be obtained by using main aqueous solution of sodium lactate and adding trimethylglycine in a limit in which ammonium-poly(meth)acrylate is not crystallized to the main aqueous solution.

As the water soluble lubricant, to the main aqueous solution composed by sodium lactate, one or more kinds of aqueous solution of agent selected from the group composed by ammonium-polyacrylate, ammonium-polymethacrylate, arabian gum, polyvinylpyrrolidone, dextran and pullulan are added. In this case, when the water content of aqueous solution of sodium lactate is from 40 to 80% by weight, the prepared solution displays a good lubricating feature. When the water content is smaller than 40%, a penetration to the wound up part of condom is not sufficient, and when it is bigger than 80% an appearance of condom becomes white.

As the water soluble lubricant, arabian gum alone is dissolved into aqueous solution of salt of dl-pyrrolidonecarboxyllic acid. When the dissolving amount of arabian gum is from 0.5 to 8.0 wt % to aqueous solution of salt of dl-pyrrolidonecaboxyllic acid, the prepared solution shows a good lubricating feature. When it is smaller than 0.5% a lubricating feature is not sufficient, and when it is bigger than 8.0 wt % a penetration to the wound up part of condom is not sufficient.

As the water soluble lubricant, pullulan alone is dissolved into aqueous solution of salt of dl-pyrrolidonecarboxylic acid. When the dissolving amount of pullulan is from 0.05 to 3.0 wt % to the aqueous solution of salt of dl-pyrrolidonecarboxylic acid, the prepared solution indicates good lubricating feature. When it is smaller than 0.05%, a lubricating feature is not sufficient, and when it is bigger than 3.0 wt %, a penetration to the wound up part of condom is not sufficient.

As the water soluble lubricant, furcelleran alone is dissolved in aqueous solution of salt of dl-pyrrolidonecarboxylic acid. When the dissolving amount of furcelleran is from 0.2 to 6.0 wt % to aqueous solution of salt of dl-pyrrolidonecarboxyllic acid, the prepared solution indicates good lubricating feature. When it is smaller than 0.2%, a lubricating feature is not sufficient and when it is bigger than 6.0 wt %, a penetration to the wound up part of condom is not sufficient.

As the water soluble lubricant, sodium-starch-glycollic acid alone is dissolved in aqueous solution of salt of dl-pyrrolidonecarboxylic acid. When the dissolving amount of sodium-starch-glycolic acid is from 0.2 to 6.0 wt % to aqueous solution of salt of dl-pyrrolidonecarboxyllic acid, the prepared solution shows a good lubricating feature. When it is smaller than 0.2%, a lubricating feature is not sufficient and when it is bigger than 6.0 wt %, a penetration to the wound up part of condom is not sufficient.

As the water soluble lubricant, it is confirmed that by adding to the main aqueous solution composed by monosaccharide, at least one kind of aqueous solution of agent selected from the group composed by arabian gum, polyvinylpyrrolidone, dextran and pullulan a lubricant having good lubricating feature can be obtained.

As the water soluble lubricant, at least one kind of agent selected from the group composed by arabian gum, polyvinylpyrrolidone, dextran and pullulan is dissolved in the main aqueous solution composed by monosaccharide. When the monosaccharide solution is an aqueous solution of from 50 to 70 wt % of xylulose, glucose or fructose, it displays good lubricating feature. When the water content is smaller than 50 wt %, these monosaccharide do not dissolve in water, and when the water content is bigger than 70 wt %, the surface appearance of condom becomes white.

As the water soluble lubricant, arabian gum alone is dissolved in the main aqueous solution composed by monosaccharide. When the dissolving amount of arabian gum is from 0.5 to 8.0 wt % to the aqueous solution of monosaccharide, the prepared solution indicates good lubricating feature. When it is smaller than 0.5%, a lubricating feature is not sufficient and when it is bigger than 8.0 wt %, a penetration to a wound part of condom is not sufficient.

As the water soluble lubricant, polyvinylpyrrolidone alone is dissolved in aqueous solution mainly composed by monosaccharide. When the dissolving amount of polyvinylpyrrolidone is from 0.5 to 8.0 wt % to aqueous solution of monosaccharide, the prepared solution displays good lubricating feature. When it is smaller than 0.5%, a lubricating feature is not sufficient and when it is bigger than 8.0 wt %, a penetration to the wound up part of condom is not sufficient.

As the water soluble lubricant, dextran alone is dissolved in the main aqueous solution composed by monosaccharide. When the dissolving amount of dextran is from 0.5 to 8.0 wt % to aqueous solution of monosaccharide, the prepared solution shows good lubricating feature. When it is smaller than 0.5%, a lubricating feature is not sufficient and when it is bigger than 8.0 wt %, a penetration to the wound up part of condom is not sufficient.

As the water soluble lubricant, pullulan alone is dissolved in the main aqueous solution composed by monosaccharide. When the dissolving amount of pullulan is from 0.05 to 3.0 wt % to aqueous solution of monosaccharide, the prepared solution shows good lubricating feature. When it is smaller than 0.05 wt %, a lubricating feature is not sufficient and when it is bigger than 3.0 wt %, a penetration to a wound up part of condom is not sufficient.

As the water soluble lubricant, it is confirmed that by adding at least one kind of aqueous solution of agent selected from the group composed by arabian gum, polyvinylpyrrolidone, dextran and pullulan to the main aqueous solution composed by sugar-alcohols, a lubricant having good lubricating feature can be obtained.

As the water soluble lubricant, at least one kind of agent selected from a group composed by arabian gum, polyvinylpyrrolidone, dextran and pullulan is dissolved into the main aqueous solution composed by sugar-alcohols. When the sugar-alcohols solution is an aqueous solution of xylitol whose water content is from 45 to 70 wt % or an aqueous solution of sorbitol whose water content is from 30 to 70 wt % or an aqueous solution of marutitol whose water content is from 35 to 70 wt %, it displays good lubricating feature. When the water content is smaller than 45 wt % in the case of xylitol or smaller than 30 wt % in the case of sorbitol or smaller than 35 wt % in the case of marutitol, the penetration to the wound up part of condom is not sufficient and when they are bigger than 70 wt %, a surface appearance of condom becomes white.

As the water soluble lubricant, arabian gum alone is dissolved into the main aqueous solution composed by sugar-alcohols. When the dissolving amount of arabian gum is from 0.5 to 8.0 wt % to aqueous solution of sugar-alcohols, the prepared solution displays good lubricating feature. When it is smaller than 0.5 wt %, a lubricating feature is not sufficient and when it is bigger than 8.0 wt %, a penetration to the wound up part of condom is not sufficient.

As an embodiment of the water soluble lubricant, dextran alone may be dissolved into main aqueous solution composed by sugar-alcohols. When the dissolving amount of dextran is from 0.5 to 8.0 wt % to aqueous solution of sugar-alcohols, the prepared solution shows good lubricating feature. When it is smaller than 0.5 wt %, a lubricating feature is not sufficient, and when it is bigger than 8.0 wt %, a penetration to the wound up part of condom is not sufficient.

As another embodiment of the water soluble lubricant, pullulan alone may be dissolved into main aqueous solution composed by sugar-alcohols. When the dissolving amount of pullulan is from 0.5 to 8.0 wt % to aqueous solution of sugar-alcohols, the prepared solution shows good lubricating feature. When it is smaller than 0.5%, a lubricating feature is not sufficient and when it is bigger than 8.0 wt %, a penetration to a wound up part of condom is not sufficient.

As another embodiment of the water soluble lubricant, it is confirmed that by the main aqueous solution composed by sodium dl-malate and at least one kind of aqueous solution of agent selected from the group composed by ammonium-polyacrylate, ammonium-polymethylacrylate, sodium polyacrylate, arabian gum, dextran and pullulan a lubricant having good lubricating feature can be obtained.

As the water soluble lubricant according to this embodiment, at least one kind of agent selected from ammonium-polyacrylate, ammonium-polymethacrylate, sodium polyacrylate, arabian gum, dextran and pullulan is dissolved into the aqueous solution composed by sodium dl-malate. When the water content of aqueous solution of sodium dl-malate is from 50 to 70% by weight, it shows a good lubricating feature. When the water content is smaller than 50 wt %, sodium dl-malate does not dissolve in water and when it is bigger than 70 wt %, a surface appearance of a condom becomes white.

As the water soluble lubricant, ammonium-polyacrylate alone may be dissolved into the main aqueous solution composed by sodium dl-malate. When the dissolving amount of ammonium-polyacrylate is from 0.1 to 3.0 wt % to aqueous solution of sodium dl-malate, the prepared solution shows good lubricity. When it is smaller than 0.1 wt % lubricity is not sufficient and when it is bigger than 3.0 wt %, a sufficient penetration to a wound up part of condom can not be obtained.

As the water soluble lubricant, ammonium-polymethacrylate alone may be dissolved into the main aqueous solution composed by sodium dl-malate. When the dissolving amount of ammonium-polymethacrylate is from 0.05 to 2.5 wt % to the aqueous solution of sodium dl-malate, the prepared solution shows good lubricity. When it is smaller than 0.05 wt %, lubricity is not sufficient and when it is bigger than 2.5 wt %, a sufficient penetration to the wound up part of condom cannot be obtained.

As the water soluble lubricant, sodium-polyacrylate alone may be dissolved into the main aqueous solution composed by sodium dl-malate. When the dissolving amount of sodium-polyacrylate is from 0.1 to 3.0 wt % to the aqueous solution of sodium dl-malate, the prepared solution shows good lubricity. When it is smaller than 0.1 wt %, lubricity is not sufficient and when it is bigger than 3.0 wt %, a sufficient penetration to the wound up part of condom can not be obtained.

As the water soluble lubricant, arabian gum alone may be dissolved into the aqueous solution composed by sodium dl-malate. When the dissolving amount of arabian gum is from 0.5 to 8.0 wt % to the aqueous solution of sodium dl-malate, the prepared solution shows good lubricity. When it is smaller than 0.5 wt %, lubricity is not sufficient and when it is bigger than 8.0 wt %, a sufficient penetration to the wound up part of condom can not be obtained.

As the water soluble lubricant, dextran alone may be dissolved into the main aqueous solution composed by sodium dl-malate. When the dissolving amount of dextran is from 0.5 to 8.0 wt % to the aqueous solution of sodium dl-malate, the prepared solution shows good lubricity. When it is smaller than 0.5 wt %, lubricity is not sufficient and when it is bigger than 8.0 wt %, a sufficient penetration to the wound up part of condom can not be obtained.

As the water soluble lubricant, pullulan alone may be dissolved into the main solution composed by sodium dl-malate. When the dissolving amount of pullulan is from 0.05 to 3.0 wt % to the aqueous solution of sodium dl-malate, the prepared solution shows good lubricity. When it is small than 0.05 wt %, lubricity is not sufficient and when it is bigger than 3.0 wt %, a sufficient penetration to the wound up part of condom can not be obtained.

As still another embodiment of the water soluble lubricant, it is confirmed that by dissolving at least one kind of aqueous solution of agent selected from the group composed by arabian gum, dextran and pullulan into the main aqueous solution composed by a mixture composed at least by two kinds of agents selected from sodium lactate, trimethylglycine, salt of dl-pyrrolidone-carboxylic acid, monosaccharide, sodium dl-malate and sugar-alcohols, a lubricant having good lubricity can be obtained.

As the water soluble lubricant, it is confirmed that by dissolving at least one kind of aqueous solution of agent selected from a group composed by ammonium polyacrylate and ammonium polymethacrylate (which may be collectively referred to as poly(meth)acrylate) into the main aqueous solution composed by a mixture of sodium lactate and sodium dl-malate, a lubricant having good lubricity can be obtained.

As the water soluble lubricant, it is confirmed that by dissolving polyvinylpyrrolidone into the main aqueous solution composed by a mixture composed at least by two kinds of agent selected from sodium lactate, monosaccharide and sugar-alcohol, a lubricant having excellent lubricity can be obtained.

When a water soluble penetrating agent to the wound up part of condom or a water soluble sliminess agent are obtained by mixing a plurality of such agents, it is confirmed that by controlling the mixing ratio of each agent within the region from 0 (zero) to the maximum soluble amount of single use of each agent, a lubricant having good penetration to the wound up part of condom and good sliminess can be obtained.

Further, the inventor of this invention, has confirmed that the plural types of water soluble lubricant which have good penetrating effect to the wound up part of condom, good wettability and sliminess can be prepared by mixing or dissolving a humectant which provides good wettability and reduces the discomfortability of using a condom, with a penetrating agent which penetrates easily into the wound up part of a condom and does not whiten the surface of a condom and a sliminess agent which provides a condom with sliminess, by the conditions mentioned below.

As the water soluble penetrating agent to the wound up part of condom, sodium lactate, trimethylglycine, sodium dl-malate, monosaccharide, salts of dl-pyrrolidonecarboxylic acid and sugar-alcohol can be used, especially sodium lactate and trimethylglycine are preferably used. The aqueous solution composed by at least one kind of said agents is used. As the water soluble sliminess agent, pullulan, ammonium polyacrylate, ammonium polymethacrylate, arabian gum, dextran, tamarindo gum, furcelleran, starch: sodium glycollic acid, sodium polyacrylate, polyvinylpyrrolidone and others can be mentioned and especially pullulan is preferably used. The aqueous solution composed by at least one kind of said agents is used. And as the humectant, glycerin, propyleneglycol and polyethyleneglycol of 200 to 600 average molecule weight are preferably used, and the aqueous solution composed by at least one kind of said agents is used.

As the water soluble lubricant, a main aqueous solution composed by sodium lactate to which at least one kind of agent selected from glycerin, propyleneglycol and polyethyleneglycol of 200 to 600 average molecule weight are added as a humectant is used. Pullulan is dissolved into said main aqueous solution, and in this case, when the water content of mixed solution of sodium lactate and humectant is from 40 to 70%, the mixture shows very good lubricating effect. However, when the water content is smaller than 40 wt %, the penetration to the wound up part of a condom is not sufficient, and when it is bigger than 70 wt % the surface appearance of a condom becomes white.

As a water soluble lubricant, a main aqueous solution composed by trimethylglycine to which at least one kind of agent selected from glycerin and propyleneglycol are added as a humectant is used. Pullulan is dissolved into the main aqueous solution, and in this case, when the water content of mixed solution of trimethylglycine and humectant is from 40 to 70%, the mixture shows very good lubrication. However, when the water content is smaller than 40 wt %, the penetration to the wound up part of a condom is not sufficient, and when it is bigger than 70 wt % the surface appearance of a condom becomes white.

As a water soluble lubricant, glycerin alone may be added as a humectant to the aqueous solution of sodium lactate, and in this case, when the added amount is from 5 to 50 wt % to the aqueous solution of sodium lactate, the mixture shows very good wettability. However, when the mixing ratio is smaller than 5 wt %, the wettability is not sufficient, and when it is bigger than 50 wt %, the penetration to the wound up part of a condom is not sufficient.

As a water soluble lubricant, glycerin alone may be mixed with the aqueous solution of trimethylglycine, and in this case, when the added amount is from 5 to 50 wt % to the aqueous solution of trimethylglycine, the mixture shows very good wettability. However, when the mixing ratio is smaller than 5 wt %, the wettability is not sufficient, and when it is bigger than 50 wt %, the penetration to the wound up part of a condom is not sufficient.

As a water soluble lubricant, propyleneglycol alone may be mixed with the aqueous solution of sodium lactate, and in this case, when the added amount is from 5 to 50 wt % to the aqueous solution of sodium lactate, the mixture shows very good wettability. However, when the mixing ratio is smaller than 5 wt %, the wettability is not sufficient, and when it is bigger than 50 wt %, the penetration to the wound up part of a condom is not sufficient.

As a water soluble lubricant, propyleneglycol alone may be mixed with the aqueous solution of trimethylglycine, and in this case, when the added amount is from 5 to 50 wt % to the aqueous solution of trimethylglycine, the mixture shows very good wettability. However, when the mixing ratio is smaller than 5 wt %, the wettability is not sufficient, and when it is bigger than 50 wt %, the penetration to the wound up part of a condom is not sufficient.

As the water soluble lubricant, a main aqueous solution composed by sodium lactate to which at least one kind of agent selected from glycerin, propyleneglycol and polyethyleneglycol of 200 to 600 average molecule weight are added as a humectant is used. Pullulan is dissolved in said aqueous solution, and in this case, when the dissolving amount is from 0.5 to 5.0 wt % to the aqueous solution composed by sodium lactate and a humectant, the mixture shows an excellent lubricating effect. However, when the dissolving ratio is smaller than 0.5 wt %, the penetration to the wound up part of a condom is not sufficient, and when it is bigger than 5.0 wt % the penetration to the wound up part of a condom is not sufficient.

As the water soluble lubricant, a main aqueous solution composed by trimethyglycine to which at least one kind of agent selected from glycerin, propyleneglycol and polyethyleneglycol of 200 to 600 average molecule weight are added as a humectant is used. Pullulan is dissolved in said aqueous solution, and in this case, when the dissolving amount is from 0.5 to 5.0 wt % to the aqueous solution composed by trimethylglycine and a humectant, the mixture shows an excellent lubricating effect. However, when the dissolving ratio is smaller than 0.5 wt %, the penetration to the wound up part of a condom is not sufficient, and when it is bigger than 5.0 wt % the penetration to the wound up part of a condom is not sufficient.

When a water soluble penetrating agent to the wound up part of condom or a humectant are composed by mixing a plurality of agents, it is confirmed that by controlling the mixing amount of each agent within the region from 0 (zero) to the maximum soluble amount of single use of these agents, a lubricant having good penetration to the wound up part of condom and good wettability can be obtained.

EXAMPLES

The invention will be understood more readily with reference to the following Examples, however these Examples are intended to illustrate the invention and are not to be construed to limit the scope of the invention.

Example 1

Table 1 to 9 show the results from confirmation experiments of the penetration effect to the wound up part of condom referring to the water soluble lubricant for condom of this invention, and in Table 1 a mixing ratio of the penetration agents used in each experiment with the sliminess agent are indicated.

Table 2, 3, 4, 5, 6, 7 and 8 show the number of days to penetrate into the wound up part of condom of lubricants which uses as a penetration agent an aqueous solution of sodium lactate (Table 2), trimethylglycine (Table 3), mixture of sodium lactate and trimethylglycine (Table 4), sodium dl-pyrrolidonecarboxylic acid (Table 5), xylose (Table 6), xylitol (Table 7) and sodium dl-malate (Table 8) and to which a sliminess agent is preferably added.

TABLE 1

| penetrating agent sliminess agent | sodium lactate | trimethyl glycine | salt of dl-pyrrolidone carboxylic acid | sodium dl-malate | monosaccharide | sugar-alcohol |
|---|---|---|---|---|---|---|
| pullulan | ○ | ○ | ○ | ○ | ○ | ○ |
| alumonium polyacrylate | ○ | | | ○ | | |
| ammonium polymethacrylate | ○ | | | ○ | | |
| sodium polyacrylate | | | | ○ | | |
| arabian gum | ○ | ○ | ○ | ○ | ○ | ○ |
| dextran | ○ | ○ | ○ | ○ | ○ | ○ |
| polyvinyl pyrollidone | ○ | | | | ○ | ○ |
| taramind gum | | | ○ | | | |
| furcelleran | | | ○ | | | |
| sodium-starch glycolic acid | | | ○ | | | |

Remarks ○ mark; preferred combinations, salt of dl-pyrollidone carboxylic acid: sodium dl-pyrollidone carboxylic acid and triethanolamine dl-pyrollidone carboxylic acids monosaccharide: xylose, glucose and fructose; sugar alcohols: xylitol, sorbitol and martitol

TABLE 2

| penetration agent | 50% aqueous solution of sodium lactate 100 gr | | | | | |
|---|---|---|---|---|---|---|
| sliminess agent | 30% ammonium polyacrylate 2 gr | 15% ammonium polymethacry-late 1.3 gr | arabian gum 2 gr | polyvinyl pyrrollidone m.w = 40000 2 gr | dextran m.w = 40000 2 gr | pullulan m.w = 200000 1 gr |
| ★ | 40 days | 40 days | 40 days | 40 days | 40 days | 30 days |

TABLE 3

| penetration agent | 50% aqueous solution of trimethylglycine 100 gr | | |
|---|---|---|---|
| sliminess agent | arabian gum 5 gr | dextran m. w ≈ 40000 4 gr | pullulan m. w ≈ 200000 1.5 gr |
| ★ | 40 days | 30 days | 30 days |

Table 4

| penetration agent | 50% aqueous solution of sodium lactate 92 gr 50% aqueous solution of trimethylglycine 8 gr | |
|---|---|---|
| sliminess agent | 30% ammonium polyacrylate 2 gr | 15% ammonium polymethacrylate 1.3 gr |
| ★ | 30 days | 30 days |

TABLE 5

| penetration agent | 50% aqueous solution of dl-pyrrolidone-carboxylic acid 100 gr | | | | | |
|---|---|---|---|---|---|---|
| sliminess agent | arabian gum 4 gr | dextran m.w = 40000 4 gr | pullulan m.w = 200000 1 gr | tamarindo gum 0.3 gr | furcelleran 1 gr | sodium starch · glycolic acid 1 gr |
| ★ | 40 days | 50 days | 40 days | 40 days | 30 days | 30 days |

TABLE 6

| penetration agent | 45% aqueous solution of xylose 100 gr | | | |
|---|---|---|---|---|
| sliminess agent | arabian gum 4 gr 15 days | polyvinyl pyrollidone m. w ≈ 40000 4 gr 15 days | dextran m. w ≈ 40000 4 gr 15 days | pullulan m. w ≈ 200000 0.5 gr 15 days |
| ★ | | | | |

TABLE 7

| penetration agent | 50% aqueous solution of xylitol 100 gr | | | |
|---|---|---|---|---|
| sliminess agent | arabian gum 4 gr 30 days | polyvinyl pyrollidone m. w ≈ 40000 4 gr 30 days | dextran m. w ≈ 40000 4 gr 30 days | pullulan m. w ≈ 40000 0.5 gr 30 days |
| ★ | | | | |

TABLE 8

| penetration agent | 45% aqueous solution of sodium dl-malate 100 gr | | | | | |
|---|---|---|---|---|---|---|
| sliminess agent | 30% ammonium polyacrylate 2 gr | 15% ammonium polymethacrylate 1.3 gr | sodium polyacrylate 0.5 gr | arabian gum 4 gr | dextran m.w = 40000 4 gr | pullulan m.w = 200000 0.5 gr |
| ★ | 50 days | 50 days | 50 days | 50 days | 50 days | 50 days |

TABLE 9

[comparative date]

dimethyl polysiloxane type silicone oil
(viscosity 100 centi stoke)
★60 days

Remark ★: number of days to penetrate into a wound up part of condom

These results show that the lubricants of this invention can remarkably decrease the number of days to penetrate into the wound up part of condom compared with the conventional lubricant composed by lipophilic type agents such as silicone oil.

Example 2

Table 10 to 12 show the results from confirmation experiments of the penetration effect to the wound up part of condom referring to the water soluble lubricant for condom of this invention.

Table 10 and 11 show the number of days to penetrate into the wound up part of condom of lubricants which uses an aqueous solution of sodium lactate (Table 10) and trimethylglycine (Table 11) as a penetration agent, to which glycerin and propyleneglycol as a humectant and pullulan as a sliminess agent are added. Table 12 shows the results by comparative experiment using silicone oil as a lubricant.

TABLE 10

| penetration agent | 40% aqueous solution of sodium lactate 100 gr | |
|---|---|---|
| sliminess agent | pullulan (m. w ≈ 200000) 2.5 gr | |
| humectant | glycerin 20 gr | propyleneglycol 20 gr |
| ★ | 40 days | 40 days |

TABLE 11

| penetration agent | 40% aqueous solution of trimethylglycine 100 gr | |
|---|---|---|
| sliminess agent | pullulan (m. w ≈ 200000) 2.5 gr | |
| humectant | glycerin 20 gr | propyleneglycol 20 gr |
| ★ | 30 days | 30 days |

TABLE 12

[comparative data]

dimethyl polysiloxane type silicone oil
(viscosity 100 centi stoke)
★ 60 days

Remark ★: number of days to penetrate into a wound up part of condom

These results show that the lubricants of this invention can remarkably decrease the number of days to penetrate into the wound up part of condom compared with the conventional lubricant composed by an oily type agent such as silicone oil.

EFFECT OF THE INVENTION

As explained in the detailed description of the invention and Examples, by combining a water soluble penetrating agent which has good penetration to the wound up part of condom, a humectant which provides a condom with good wettability and a water soluble sliminess agent which provide a condom with sliminess at actual use, a water soluble lubricant for condom which can be easily removed by water when adhered to skin, does not whiten the appearance of a condom, further has a good penetration to the wound up part of condom, and a condom whose surface is spread with said water soluble lubricant can be prepared.

What is claimed is:

1. A water soluble lubricant consisting essentially of
   A) at least one sliminess agent selected from the group consisting of pullulan, ammonium poly(meth)acrylate, arabian gum, dextran, tamarindo gum, furcelleran, sodium starch-glycollic acid, sodium polyacrylate, and polyvinyl pyrrolidone; and
   B) at least one penetrating agent selected from the group consisting of sodium lactate, trimethylglycine, sodium dl-malate, monosaccharide, salt of dl-pyrrolidonecarboxylic acid and sugar alcohol.

2. The water soluble lubricant according to claim 1 which further contains
   C) at least one humectant selected from the group consisting of glycerin, propylene glycol and ethylene glycol of 200 to 600 average molecular weight.

3. A lubricated condom comprising on the surface thereof the water-soluble lubricant of claim 1 or claim 2.

4. A method for imparting lubricity, adequate slipperiness and sliminess to a condom which comprises applying to the surface of the condom a water soluble lubricant of claim 1 or 2.

5. A wound lubricated condom having on the surface thereof a water soluble lubricant comprising at least one kind of sliminess agent selected from the group consisting of pullulan, ammonium polyacrylate, ammonium-poly(meth)acrylate, arabian gum, dextran, tamarindo gum, furcelleran, sodium-starch-glycollic acid and sodium polyacrylate, and a penetrating agent.

6. The wound lubricated condom having on the surface thereof a water soluble lubricant of claim 5, wherein the penetrating agent is at least one agent selected from the group consisting of sodium-lactate, trimethylglycine, sodium dl-malate, monosaccharide, salt of dl-pyrrolidonecarboxylic acid and sugar alcohol.

7. A wound lubricated condom having on the surface thereof a water soluble lubricant comprising at least one kind of penetrating agent selected from the group consisting of by sodium lactate, trimethylglycine, sodium dl-malate, monosaccharide, salt of dl-pyrrolidonecarboxylic acid and sugar alcohol, and a sliminess agent.

8. The wound lubricated condom having on the surface thereof a water soluble lubricant of claim 7, wherein the sliminess agent is at least one agent selected from the group consisting of pullulan, ammonium poly(meth)acrylate, arabian gum, dextran, tamarindo gum, furcelleran, sodium-starch glycollic acid and sodium polyacrylate.

9. A wound lubricated condom having on the surface thereof a water soluble lubricant consisting essentially of
   A) at least one sliminess agent selected from the group consisting of pullulan, ammonium poly(meth)acrylate, arabian gum, dextran, tamarindo gum, furcelleran, sodium starch-glycollic acid and sodium polyacrylate; and
   B) at least one penetrating agent selected from the group consisting of sodium lactate, trimethylglycine, sodium dl-malate, monosaccharide, salt of dl-pyrrolidonecarboxylic acid and sugar alcohol.

10. A method for imparting lubricity, adequate slipperiness and sliminess to a wound condom which comprises applying to the surface of the wound condom a lubricating agent of claim 9.

11. A wound lubricated condom having on the surface thereof a water soluble lubricant consisting essentially of
   A) at least one sliminess agent selected from the group consisting of pullulan, ammonium poly(meth)acrylate, arabian gum, dextran, tamarindo gum, furcelleran, sodium starch-glycollic acid and sodium polyacrylate;
   B) at least one penetrating agent selected from the group consisting of sodium lactate, trimethylglycine, sodium dl-malate, monosaccharide, salt of dl-pyrrolidonecarboxylic acid and sugar alcohol; and
   C) at least one humectant selected from the group consisting of glycerin, propylene glycol and ethylene glycol of 200 to 600 average molecular weight.

12. A wound lubricated condom having on the surface thereof a water soluble lubricant consisting essentially of
   A) at least one sliminess agent selected from the group consisting of pullulan, ammonium poly(meth)acrylate, arabian gum, tamarindo gum, furcelleran, sodium starch-glycollic acid and sodium polyacrylate; and
   B) at least one penetrating agent selected from the group consisting of sodium lactate, trimethylglycine, sodium dl-malate, salt of dl-pyrrolidonecarboxylic acid and sugar alcohol.

* * * * *